United States Patent [19]

Thomas

[11] 4,106,926

[45] Aug. 15, 1978

[54] SINTERED HERBICIDE-FILLED CELLULOSE ESTER PARTICLES HAVING IMPROVED RESISTANCE TO WATER LEACHING

[75] Inventor: Norman W. Thomas, Warren, N.J.

[73] Assignee: Celanese Corporation, New York, N.Y.

[21] Appl. No.: 791,763

[22] Filed: Apr. 28, 1977

[51] Int. Cl.$^2$ .......................... A01N 9/24; A01N 9/20
[52] U.S. Cl. ...................................... 71/115; 71/64 F; 71/DIG. 1
[58] Field of Search ................... 71/DIG. 1, 115, 64 F

[56] References Cited

U.S. PATENT DOCUMENTS

| | | | |
|---|---|---|---|
| 3,013,873 | 12/1961 | Hart et al. | 71/111 X |
| 3,014,063 | 12/1961 | McLane et al. | 71/111 X |
| 3,172,752 | 3/1965 | Pierce | 71/79 X |
| 3,318,769 | 5/1967 | Folckemer | 424/81 X |
| 3,328,256 | 6/1967 | Gaunt | 71/DIG. 1 |
| 3,336,155 | 8/1967 | Rowe | 8/79 X |
| 3,560,196 | 2/1971 | Horai et al. | 71/115 |

OTHER PUBLICATIONS

Stokes, et al., J. Agr. Food Chem., vol. 21, 1973, pp. 103–108.

*Primary Examiner*—Joseph Paul Brust

[57] ABSTRACT

A controlled-release composition comprising discrete particles of water-leachable herbicide occupying the voids, or channels, of a particulate, substantially water-impermeable, porous, cellulose ester carrier is provided with enhanced resistance to water leaching of the herbicide component thereof following sintering of the herbicide contained in the composition.

The herbicide-filled cellulose ester composition can be prepared by the method which comprises:
a. dissolving cellulose ester in a solvent;
b. combining the cellulose ester solution with a sufficient amount of a liquid which is non-solvent for cellulose ester, but miscible with the cellulose ester solvent, under vigorous agitation to provide a homogeneous liquid containing porous cellulose ester particles having voids, or channels, communicating with the exterior surface thereof;
c. contacting the cellulose ester particles with a water-leachable herbicide having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;
d. drying the cellulose ester particles; and
e. heating the dried herbicide-filled cellulose ester particles at the sintering temperature of the herbicide but below the softening temperature of the cellulose ester.

The herbicidal composition can also be prepared by the leaching and pulverizing method as fully disclosed in the description of the preferred embodiments herein.

14 Claims, No Drawings

SINTERED HERBICIDE-FILLED CELLULOSE ESTER PARTICLES HAVING IMPROVED RESISTANCE TO WATER LEACHING

BACKGROUND OF THE INVENTION

1. Field of the Invention

This invention relates to the field of water-leachable pre-emergence herbicidal compositions which are characterized by controlled release of the herbicide contained in the composition on exposure to moisture.

2. Description of the Prior Art

Herbicides are substances used to destroy plants, especially weeds, or to check their growth. Commonly, for weed control in agriculture, water soluble herbicides are employed in the soil to prevent the emergence of undesired plants, e.g., weeds, which compete with desired plants. Such herbicides are referred to as pre-emergence herbicides and are usually dependent on rain or irrigation to wash the herbicide into the soil. Due to variable rainfall, the efficiency of washing such herbicides into the soil poses a difficult problem in that with increased rainfall the extent of penetration into the soil layer by the herbicide may be excessive with highly soluble herbicides, i.e., the herbicide is leached to a zone below that in which the undesired, i.e., weed, seeds are germinating. The result is an unsatisfactory weed control. In addition to the solubility problem, penetration differentials are also attributable to the type of soil, i.e., sandy, loose soil versus muck soil, and, importantly, the relative ability of the soil components to absorb the herbicide. It is apparent that the success of weed control among agricultural crops such as beans and tomatoes with pre-emergence herbicides is a complex problem which must entail consideration of the soil, crop, weed and environmental conditions, especially rainfall.

In addition to the problem of leaching the herbicide to below the zone of weed seed germination, is the problem generated by excessively long residence time of the herbicide in the upper zones of the soil where, on a protracted basis, adverse effects of the herbicide can occur with respect to the germination of desired seeds, or alternatively with respect to established plants or trees. Thus, the leachability of the herbicide must permit adequate penetration to the soil zone where weed seeds are germinating but at the same time should be sufficient to remove the herbicide from the growth zone within reasonable periods of time. Ideally, the herbicide should have a leachability which would permit effective presence only during the germination period of the undesired seeds, after which the herbicide is effectively removed from the growth zones of the soil.

Banvel is a known pre-emergence herbicide which is of high water solubility. This commercial product, however, suffers from the aforesaid difficulties when employed in the soil, primarily because of water-solubility, i.e., heavy rain may leach the herbicide below the zone of weed seed germination. Banvel also is not as readily adsorbed by the soil as are other pre-emergence herbicides, in which event the leaching rate of Banvel in sandy soil and clay loam soil is substantially the same, as evidenced by the relatively small changes in leaching rates required to obtain similar weed control in both sandy and clay laom soil. Even in muck soil, Banvel appears to move rather readily through the soil profile. Other herbicides, such as Diuron, CIPC and PCP require several fold changes in rate to produce similar herbicidal effect with broad changes in the soil types.

U.S. Pat. No. 3,336,155 describes the coating of solid and liquid particles with polymers separated from an organic solvent solution thereof by the addition, under stirring, of an organic liquid which is a non-solvent for the solid or liquid particles which must be insoluble in the miscible solvent and non-solvents. Among the numerous polymers and materials to be coated recited in U.S. Pat. No. 3,336,155 are cellulose acetate and the water soluble herbicide, sodium (2,4-dichlorophenoxy) acetate.

U.S. Pat. No. 3,318,769 describes a thermoplastic resin such as cellulose acetate having dissolved therein up to about 70% by weight of a water insoluble dialkyl beta-halogen substituted vinyl phosphate insecticide. In some cases, the solid solutions are heated up to about 100° C or higher to achieve solidification of the resin. The insecticides diffuse through, and evaporate from, the resin into the surrounding atmosphere over an extended period.

Commonly assigned copending U.S. patent application Ser. No. 791,823 filed Apr. 28, 1977 describes compositions of a benzoic acid pre-emergence herbicide in a matrix of cellulose ester which ameliorates the problem of excessive leaching by water while still providing effective levels of the herbicide for control of undesired seed germination as well as weed growth after germination.

The benzoic acid pre-emergence herbicides are well known compounds and have been described in the patent literature (See U.S. Pat. Nos. 3,014,063 and 3,013,873).

Banvel is particularly characteristic of the benzoic acid-herbicides which are especially affected by water solubility and, consequently, the problem of excessive leaching by water, e.g., rainfall, in the soil. The known class of benzoic acid herbicides includes mono-, di- and tri-substituted benzoic acids, in which the substituents are halo, amino, nitro, lower alkoxy. The most effective of such derivatives are the tri-substituted benzoic acid herbicides, particularly those containing chloro substituents. Thus, Banvel is 2-methoxy-3,6-dichlorobenzoic acid; another commercial herbicide, Amiben, is 3-amino-2,5-dichlorobenzoic acid. Other such herbicides include, for example, trichloro-benzoic acid; 3-nitro-2,5-dichlorobenzoic acid (Dinoben) and similar such tri-substituted benzoic acids.

SUMMARY OF THE INVENTION

The controlled release and enhanced resistance to water leaching obtainable with the sintered compositions of this invention provide desirable levels of the herbicide in the ambient soil to provide significant herbicidal action. In addition to obvious benefits, the present new compositions minimize the danger of contamination of underground water supplies by significant levels of the herbicide. The results obtained with Banvel, a widely used benzoic acid herbicide, are quite remarkable.

As employed herein, the term "benzoic acid herbicide" is intended to include the herbicidal substituted benzoic acids and combinations thereof having a sintering temperature below the softening temperature of the cellulose ester carrier. Accordingly, relatively high melting benzoic acid herbicides such as Amiben (m.p. 201° C.) and Dinoben (m.p. 220°–221° C.) can be used in combination with relatively low melting benzoic acid herbicides such as Banvel (m.p. 114°–116° C.) and 2,3,6-trichlorobenzoic acid (m.p. 125°–126° C.) provided the combination of herbicides is capable of being sintered at a temperature below the softening temperature of the cellulose ester carrier selected. The term "sintering temperature" and terms of like import as employed herein refer to a range of temperature below the softening temperature of the cellulose ester carrier, to which the herbicide-filled cellulose ester particles are heated to significantly enhance the resistance to water leaching of the herbicide component thereof.

Broadly stated, the controlled-release herbicidal composition comprises discrete particles of water-leachable herbicide occupying the voids, or channels, of a particulate, substantially water-permeable, porous cellulose ester carrier wherein said herbicide has a sintering temperature below the softening temperature of the cellulose ester carrier and said voids, or channels, communicate with the exterior surface of the cellulose ester carrier particles, the herbicidal composition being heated at about the sintering temperature of the herbicide but below the softening temperature of the cellulose acetate.

The herbicidal composition can be prepared by the solvent separation method which comprises:

a. dissolving cellulose ester in a solvent;

b. combining the cellulose ester solution with a sufficient amount of a liquid which is a non-solvent for cellulose ester, but miscible with the cellulose ester solvent, under vigorous agitation to provide a homogeneous liquid containing porous cellulose ester particles having voids, or channels, communicating with the exterior surface thereof;

c. contacting the cellulose ester particles with a water-leachable herbicide having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;

d. drying the cellulose ester particles; and e. heating the dried herbicide-filled cellulose ester particles at the sintering temperature of the herbicide but below the softening temperature of the cellulose ester.

Alternatively, the herbicidal composition can be prepared by the method which comprises:

a. incorporating particles of a solid foreign material insoluble in cellulose ester substantially uniformly throughout a mass of cellulose ester;

b. pulverizing the cellulose ester mass to provide cellulose ester particles containing particles of solid foreign material distributed substantially uniformly throughout said particles;

c. leaching the particles of solid foreign material contained in the cellulose ester particles with a liquid which is a solvent for the foreign material but a non-solvent for the cellulose ester to provide porous cellulose ester particles having voids, or channels, communicating with the exterior surface of said particles;

d. contacting the cellulose ester particles with a water-leachable herbicide having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;

e. drying the cellulose ester particles; and f. heating the dried herbicide-filled cellulose ester particles at the sintering temperature of the herbicide but below the softening temperature of the cellulose ester.

It is also within the scope of this invention to leach the particles of solid foreign material from the cellulose ester mass prior to the pulverization of the latter.

DESCRIPTION OF THE PREFERRED EMBODIMENTS

Banvel and the trichlorobenzoic acids are especially preferred benzoic acid herbicides for use herein since they possess a sintering temperature well below the softening temperature of the preferred cellulose ester, cellulose acetate (160°–170° C.). Benzoic acid herbicides having melting points above the softening temperature of the cellulose ester carrier cannot be used by themselves. However, mixtures of benzoic acid herbicides having a sintering temperature below the softening temperature of the cellulose ester can be used even though one or more of the component herbicides by itself possesses a sintering temperature which is in excess of the tolerable limit.

While the following is referenced principally to the use of the preferred cellulose ester, cellulose acetate, it is understood that other cellulose esters such as cellulose propionate, cellulose acetate butyrate, and the like can also be employed as the herbicide carrier.

The cellulose acetate herein is soluble in such common organic solvents as ketones, esters and other known and conventional cellulose acetate solvents. Thus, for example, cellulose acetate can be dissolved in a suitable ketone solvent such as acetone, methyl ethyl ketone, 2-pentanone, 3-pentanone, 2-hexanone, 3-hexanone, methyl isobutyl ketone, cycylohexanone, acetophenone, benzophenone, an ester such as ethyl acetate, ethyl propionate, ethyl butyrate, ethyl isobutyrate, propyl acetate, propyl butyrate, butyl acetate, butyl butyrate, amyl acetate, or a cyclic ether such as 1,4-dioxane. Mixtures of cellulose acetate solvents can also be advantageously employed herein. The optimum amount of solvent to be used in a given operation will depend upon such factors as the characteristics of the solvent, the nature of the cellulose ester, temperature, etc., and is readily determined by those skilled in the art using routine procedures. Excellent results have been obtained with 5% and 10% by weight solutions of cellulose acetate having an acetyl value of 55 in a 60/40 weight percent solution of acetone/formamide.

The addition to the cellulose acetate solution under vigorous agitation of a liquid which is a non-solvent for cellulose acetate, but miscible in the cellulose acetate solvent, will cause the cellulose acetate to separate from solution as low density, porous particles having voids, or channels, communicating with the exterior surface of the particles. Thus, for example, the addition of water or an alcohol such as methanol, ethanol, propanol, isopropanol, butanol, hexanol, and the like, to an acetone/formamide solution of cellulose acetate will result in the separation of porous cellulose acetate particles in a homogeneous liquid. Water is the preferred liquid herein for reasons of economy and efficiency of operation. As will be readily appreciated by those skilled in the art, the optimum amount of water or other non-solvent used will depend upon the concentration of the cellulose ester, solution, the nature of both the solvent and non-solvent, and the prevailing ambient conditions, and is readily determined employing conventional procedures.

Advantageously, the non-solvent as added to the cellulose acetate solution under high shear mixing conditions. On a laboratory scale, a Waring blender or Osterizer will provide good results. Stirring is usually of brief duration, 30 seconds providing complete separation of the cellulose acetate particles. A typical wet sieve analysis has provided cellulose acetate particles of varying particle size of which more than 80% by weight pass through a U.S. Sieve No. 20, i.e., less than 841 microns (cellulose acetate sample B of Example I, infra).

Following the separation of the porous cellulose acetate particles from the solvent, the particles can be recovered by any suitable means, for example, by decantation, filtration, or centrifugation. If desired, the particles can be washed free of any residual coagulant liquid. In any event, following separation, the porous particles should not be permitted to dry to any appreciable extent prior to being filled with herbicide since drying results in undesirable collapse and/or constriction of the voids. The wet cellulose acetate particles are then contacted with a solution of herbicide in a non-solvent for cellulose acetate. The herbicide solvent is preferably one of good solvency so that a relatively highly concentrated solution of herbicide is imbibed by the particle voids providing high herbicide loading in the particles following drying. Organic solutions of benzoic acid herbicides, e.g., methanol solutions, have provided excellent results and are preferred for use herein. When an alcohol is used as the non-solvent for the step of separating the cellulose acetate particles from solution, the herbicide can be previously dissolved in the alcohol thereby accomplishing the simultaneous separation of the cellulose acetate powder and the absorption of the herbicide into the voids of the powder.

The amount of herbicide imbibed by the cellulose acetate particles will vary largely according to the volume of the voids in the particle, and to a lesser extent, the nature of the herbicide solvent vehicle and the duration of contact of the particles with the herbicide solution. Herbicide loadings of from about 25% to 60% by weight are typical. The volume of the voids in a given quantity of cellulose acetate particles is related to the amount of urea imbibed by a two or three gram sample of the particles in 100 grams of a 45/55 weight % solution of urea/distilled water over a four hour period. Such a procedure offers a simple means for evaluating the relative porosity of a cellulose acetate particle sample. Cellulose acetate particles prepared in accordance with this invention typically imbibed from about 60% to about 75% by weight of urea. Drying of the wet cellulose acetate particles can be accomplished by any suitable method, for example, by air-drying at ambient temperature or at an elevated temperature which is below the softening point of the resin, and at ambient or subatmospheric pressure.

The sintering operation is carried out by heating the herbicide-filled cellulose acetate particles to the sintering temperature of the herbicide, a range of temperature which for most of the useful herbicides herein, generally extends from a temperature just below the melting point of the herbicide, but not in excess of the softening temperature of cellulose acetate. It is possible, however, to achieve acceptable sintering at a temperature above or below the aforesaid range. The optimum sintering temperature for a given herbicide can be readily determined by heating a series of herbicide-filled cellulose acetate particle samples at different temperatures and observing the leaching behavior of the resulting compositions. The optimum sintering temperature will, of course, be that at which the most nearly ideal leaching characteristics are obtained. Excellent results have been obtained by heating a Banvel-filled cellulose acetate to a sintering temperature within the range of from about 95° C. to about 120° C. Fluidized heating bed apparatus of known and conventional type are especially advantageous for sintering the controlled-release compositions herein. While the mechanism by which sintering of the herbicide-filled cellulose acetate powder enhances the resistance of the powder to water leaching is not known, it is speculated that the surface area of the herbicide changes with a consequent reduced tendency of the crystals to dissolve in water. This explanation of the effect of sintering is theoretical only and is not meant to limit the scope of the invention in any way.

Following the alternative method of preparing the herbicidal composition of this invention, finely-sized particles of a foreign material which is insoluble in cellulose acetate is incorporated therein. Advantageously, the foreign material is a water-leachable inorganic salt, both for reasons of economy as well as process efficiency. Thus, for example, an inorganic salt such as sodium chloride, potassium chloride, sodium carbonate, calcium chloride, and the like, of suitable particle size is substantially uniformly incorporated in a molten mass of cellulose acetate (melting point about 260° C.) or an organic solvent solution of cellulose acetate, the solvent content of the latter thereafter being evaporated. Micronized salt is advantageously employed. The amount and particle size of the salt added to the cellulose acetate will be the principal factors governing the size and quantity of the voids in the cellulose acetate following the leaching step. These factors can be readily manipulated to provide cellulose acetate particles having a predetermined degree of voidness as will be understood by those skilled in the art. Prior to, or following, pulverization of the salt-containing cellulose acetate mass in a ball mill or other known and conventional pulverizing apparatus the resulting particles are leached with water to remove the salt. Leaching of pulverized cellulose acetate is preferred since the greater exposed surface of the particles will accelerate the extraction of the salt. If an alkali metal salt is used, care must be taken to insure that virtually all of the salt is leached from the cellulose acetate powder so as to avoid any alkali contamination of the soil to which the herbicide-filled powders will eventually be applied. The salt-free porous cellulose acetate powder is contacted with a herbicide solution, dried and then sintered as in the above-described preferred procedure for preparing the herbicidal composition herein.

The following examples are illustrative of the sintered herbicide-filled cellulose acetate compositions of this invention and the methods of their preparation.

EXAMPLE I

1. Preparation of Cellulose Acetate Solutions

The following cellulose acetate (acetyl value of 55) solutions are prepared using a 60/40 weight % solution of acetone/formamide as solvent:

|  | Cellulose Acetate Solution | | | | | |
|---|---|---|---|---|---|---|
|  | A | B | C | D | E | F |
| Weight % cellulose acetate | 10 | 10 | 5 | 20 | 10 | 10 |
| Weight % solvent | 90 | 90 | 95 | 80 | 90 | 90 |
| Blending time (hours) | 16 | 16 | 16 | 16 | 18 1/4 | 17 1/6 |

2. Preparation on Porous Cellulose Acetate Particles

These solutions (in separate runs) are each injected under pressure through a Jamesbury valve, through a Monofil jet and into an Osterizer blender set at "blend".

The conditions are recorded as follows:

|  | Cellulose Acetate Particles*** | | | | |
|---|---|---|---|---|---|
| Cellulose acetate sol. | A | B | C | D | G** |
| Monofil jet, size in M | 1000 | 1000 | 400 | 1000 | 1000 |
| Dropping distance | 4 in. | 4 in. | 4 in. | 4 in. | 4 in. |
| Amt. of distilled water in Osterizer | 2¼ cups | 2¼ cups | 2¼ cups | 2¼ cups | 2¼ cups |
| Room temperature | 26° C | 24° C | 24° C | 24° C | 22° C |
| Osterizer setting | blend | blend | blend | blend | blend |
| Delivery time | 20 sec. | 20 sec. | 20 sec.* | 20 sec. | 20 sec. |
| Nitrogen pressure | 20 psig | 20 psig | 20 psig | 20 psig | 10 psig |
| No. of washes on Buchner funnel | 2 | 2 | 2 | 2 | 2 |
| Amt. of distilled water, each wash | 2¼ cups | 2¼ cups | 2¼ cups | 2¼ cups | 2¼ cups |

*The cellulose acetate solution in the jet continued to fall after the valve was closed.
**Combination of cellulose acetate solutions E and F - procedure carried out in six equal portions.
***The total amount of each cellulose acetate solution is 300 ml prepared in 50 ml portions.

3. Wet Sieve Analysis of Porous Cellulose Acetate Particles

Wet cellulose acetate particle samples B and G were sieved with the following results:

|  |  | Wt. % Retained on Sieve | |
|---|---|---|---|
| U.S. Sieve No. | Microns | B | G |
| 230 | 63 | 0.3 | 0.1 |
| 200 | 74 | 0.3 | 0.1 |
| 140 | 105 | 0.4 | 0.1 |
| 100 | 149 | 1.3 | 1.0 |
| 60 | 250 | 1.7 | 2.3 |
| 40 | 420 | 24.4 | 7.8 |
| 30 | 595 | 50.2 | 12.0 |
| 20 | 841 | 21.5 | 77.0 |

Despite the difference in sieve size distribution of cellulose acetate particle samples B and G, the samples had imbibed an average of 66% and 64%, respectively, of urea from a 45/55 weight % solution of urea/distilled water.

4. Preparation of Sintered Herbicide-Filled Cellulose Acetate Particle

Cellulose acetate particle sample G was contacted with methanol solutions of Banvel and following a period of imbibition with occasioned stirring, was dried and heated in a warm air oven at 105° C–120° C. The procedure employed is summarized as follows:

|  | Herbicide-Filled Cellulose Acetate Particles | | |
|---|---|---|---|
| (Wet) cellulose acetate particles | Run No. 1 | Run No. 2 | Run No. 3 |
| Weight % Banvel in methanol | 15 | 7.5 | 15 |
| Weight (grams) methanolic Banvel sol. | 100 | 100 | 200 |
| Weight (grams) cellulose acetate articles | 20 | 20 | 40 |
| Period of imbibition (hours) | 4.0 | 4.0 | 4.0 |
| Weight % Banvel imbibed* | 55.04 | 26.61 | 32.49 |

*As measured from % absorbance of 1,4-dioxane solution of herbicide filled particles using U.V. spectrophotometry.

EXAMPLE II

A 10% by weight solution of cellulose acetate in acetone is prepared. 35 grams of micronized sodium chloride (60 mesh) is added to 150 ml. of the cellulose acetate solution and the mixture is vigorously stirred in an Osterizer blender and quickly cast as a 16 mil thick film. After air drying, the film is ground to a powder (10–20 mesh) in a ball mill.

The powder is then leached with distilled water to dissolve the salt content thereof. The wet salt-free powder is contacted with a 10% by weight methanol solution of Banvel herbicide. After 4 hours of occasional stirring, the powder is recovered by filtration, air dried and heated in a hot air oven at 105° – 120° C. to achieve sintering.

EXAMPLE III

The controlled release of herbicide from a sintered Banvel-filled cellulose acetate particle sample prepared in accordance with this invention measured as resistance to water leaching is determined as follows:

Filter paper is placed in a 10 cm. diameter Buchner funnel, 135 ml. of dry sand mixed with sintered Banvel-filled cellulose acetate powder containing the equivalent of 20 mg. of Banvel is placed on the filter paper, a second sheet of filter paper is placed on the sand/herbicide mixture and 40 ml. of dry sand are placed on the second sheet of filter paper. The sand is extracted with 180 ml. portions of distilled water, each portion being equivalent to approximately 1 inch of rainfall. The separate extracts are analyzed by an appropriate method for Banvel. After 10 extractions, the sand and its components are transferred to a beaker and are digested with 1,4-dioxane to dissolve the polymer. The 1,4-dioxane is evaporated or made up to a known volume to be analyzed for unleached active ingredient. The identical procedure was twice repeated except that in one repeat, 20 mg. of Banvel was employed in place of sintered Banvel-filled cellulose acetate powder, and in the other repeat, unsintered Banvel-filled cellulose acetate powder was used in place of the sintered composition. The following results were recorded:

|  |  | %Leached, 10 Inch Rainfall Equivalent | |
|---|---|---|---|
| Average Particle Size (mesh) | Banvel Control | Unsintered Banvel-Filled Cellulose Acetate Powder | Sintered Banvel Filled Cellulose Acetate Powder |
| 20 mesh | 100, 98 |  |  |
| 20 mesh |  | 58, 56 |  |
| 20 mesh |  |  | 28, 33 |

In referring to voids, or channels formed in the cellulose ester structures defined herein, it is intended to comprehend pores, passageways or other internal structure contributing to surface area and the capacity of the structure to entrain, imbibe or occlude the herbicide, without limitation.

Reference has been made herein to the benzoic acid herbicides which are in some cases available in salt form e.g. as the ammonium salt whereas the present disclosure should be considered confined essentially to these herbicides employed as the free acids.

The herbicidal component will be provided to the soil over an extended term of e.g., 3 to 6 weeks or more in an effective amount for the control of undesirable plant species such as annual broad leaf and grass weeds in accordance with recommended dosage limits therefor, in respect of use in conjunction with specified cultivars such as small grains, corn, flax, perennial seed grasses, turf as well as non-crop lands. The compositions of the invention may be applied to the surface or incorporated into the soil in conventional manner.

What is claimed is:

1. A controlled-release sintered herbicidal composition comprising discrete particles of a water-leachable benzoic acid herbicide selected from the group consisting of mono-, di- and tri-substituted benzoic acids in which the substituents are halo, amino, nitro and lower alkoxy occupying the voids, or channels, of a particulate, substantially water-impermeable, porous cellulose ester carrier wherein said herbicide has a sintering temperature below the softening temperature of the cellulose ester carrier and said voids, or channels, communicate with the exterior surface of the cellulose ester carrier particles, the herbicidal composition being heated at about the sintering temperature of the herbicide but below the softening temperature of the cellulose ester.

2. The composition according to claim 1, wherein the cellulose ester is cellulose acetate.

3. The composition according to claim 1, wherein the herbicide is selected from the group consisting of 2-methoxy-3,6-dichlorobenzoic acid, 3-amino-2,5-dichlorobenzoic acid, trichloro-benzoic acid and 3-nitro-2,5-dichlorobenzoic acid.

4. The composition according to claim 1, wherein the concentration of herbicide is from about 25% to about 60% by weight of the cellulose ester carrier.

5. A method for preparing a sintered controlled-release herbicidal composition which comprises:
   a. dissolving cellulose ester in a solvent;
   b. combining the cellulose ester solution with a sufficient amount of a liquid which is a non-solvent for cellulose ester, but miscible with the cellulose ester solvent, under vigorous agitation to provide a homogeneous liquid containing porous cellulose ester particles having voids, or channels, communicating with the exterior surface thereof;
   c. containing the cellulose ester particles with a water-leachable benzoic acid herbicide selected from the group consisting of mono-, di- and tri-substituted benzoic acids in which the substituents are halo, amino, nitro and lower alkoxy having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;
   d. drying the cellulose ester particles; and
   e. heating the dried herbicide-filled cellulose ester particles at the sintering temperature of the herbicide but below the softening temperature of the cellulose ester.

6. The method according to claim 5, wherein the cellulose ester is cellulose acetate.

7. The method according to claim 5, wherein the cellulose acetate solvent is a mixture of acetone and formamide.

8. The method according to claim 6, wherein the non-solvent for cellulose acetate is water.

9. The method according to claim 5 wherein the herbicide is selected from the group consisting of 2-methoxy-3,6-dichlorobenzoic acid, 3-amino-2,5-dichlorobenzoic acid, trichloro-benzoic acid and 3-nitro-2,5-dichlorobenzoic acid.

10. The method of claim 5, wherein the concentration of herbicide in the sintered composition is from about 25% to about 60% by weight of the cellulose ester carrier.

11. The method of claim 9, wherein the sintering temperature is from about 95° C to 120° C.

12. A method for preparing a sintered controlled-release herbicidal composition which comprises:
   a. incorporating particles of a solid foreign material insoluble in cellulose ester substantially uniformly throughout a mass of cellulose ester;
   b. pulverizing the cellulose ester mass to provide cellulose ester particles containing particles of solid foreign material distributed substantially uniformly throughout said particles;
   c. leaching the particles of solid foreign material contained in the cellulose ester particles with a liquid which is a solvent for the foreign material but a non-solvent for the cellulose ester to provide porous cellulose ester particles having voids, or channels, communicating with the exterior surface of said particles;
   d. contacting the cellulose ester particles with a water-leachable benzoic acid herbicide selected from the group consisting of mono-, di- and tri-substituted benzoic acids in which the substituents are halo, amino, nitro and lower alkoxy having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;
   e. drying the cellulose ester particles; and
   f. heating the dried herbicide-filled cellulose ester particles at the sintering temperature of the herbicide but below the softening temperature of the cellulose ester.

13. A method for preparing a sintered controlled-release herbicidal composition which comprises:
   a. incorporating particles of a solid foreign material insoluble in cellulose ester substantially uniformly throughout a mass of cellulose ester;
   b. leaching the particles of solid foreign material contained in the cellulose ester mass with a liquid which is a solvent for the foreign materials but a non-solvent for the cellulose ester to provide a porous cellulose acetate mass;
   c. pulverizing the porous cellulose ester mass to provide porous cellulose ester particles having voids, or channels, communicating with the exterior surface of said particles;

d. contacting the cellulose ester particles with a water-leachable benzoic acid herbicide selected from the group consisting of mono-, di- and tri-substituted benzoic acids in which the substituents are halo, amino, nitro and lower alkoxy having a sintering temperature below the softening temperature of the cellulose ester, said herbicide being dissolved in a liquid which is a non-solvent for cellulose ester whereby the voids, or channels, of the cellulose ester particles become partially or substantially completely occupied with at least a part of the herbicide solution;

e. drying the cellulose ester particles; and f. heating the dried herbicide-filled cellulose ester particles at the sintering temperature of the herbicide but below the softening temperature of the cellulose ester.

14. A method for delivering an effective amount of a benzoic acid herbicide to a soil region for control of undesirable weed species in a controlled and sustained manner over a period of of at least 3 weeks comprising providing said herbicide to the soil in the form of granules of the composition of claim 1.

* * * * *